United States Patent [19]

Ask et al.

[11] Patent Number: 5,756,520

[45] Date of Patent: May 26, 1998

[54] COMPOUNDS WITH ANALGESIC AND LOCAL ANAESTHETIC EFFECT

[75] Inventors: Anna-Lena Ask, Huddinge; Lars-Inge Olsson, Södertälje; Rune Sandberg, Järna, all of Sweden

[73] Assignee: Astra AB, Sweden

[21] Appl. No.: 403,767

[22] PCT Filed: Feb. 3, 1995

[86] PCT No.: PCT/SE95/00106

§ 371 Date: Mar. 24, 1995

§ 102(e) Date: Mar. 24, 1995

[87] PCT Pub. No.: WO95/21821

PCT Pub. Date: Aug. 17, 1995

[30] Foreign Application Priority Data

Feb. 11, 1994 [SE] Sweden ............................ 9400447

[51] Int. Cl.$^6$ ...................... A61K 31/445; C07D 211/32
[52] U.S. Cl. .................. 514/330; 514/316; 514/326; 546/189; 546/225; 546/208; 546/234
[58] Field of Search ..................... 546/208, 234, 546/189, 225; 514/316, 326, 330

[56] References Cited

U.S. PATENT DOCUMENTS

| | | | |
|---|---|---|---|
| 2,951,080 | 8/1960 | Pohland | 260/294.3 |
| 3,850,935 | 11/1974 | Nakao et al. | 260/293.52 |

FOREIGN PATENT DOCUMENTS

| | | |
|---|---|---|
| 96980 | 8/1939 | Sweden. |
| 931789 | 7/1963 | United Kingdom. |
| WO 91/09845 | 7/1991 | WIPO. |

OTHER PUBLICATIONS

*Chemical Abstracts* 101:749, abstr. # 191709Z (1984).

Hardy et al., "Structure–Activity Relationship of Some New Analogs of Pethidine," *J. Med. Chem.* 8:847–851 (1965).

*Primary Examiner*—C. Warren Ivy
*Assistant Examiner*—Evelyn Huang
*Attorney, Agent, or Firm*—Michael A. Sanzo; Vinson & Elkins

[57] ABSTRACT

New compounds of the formula (A)

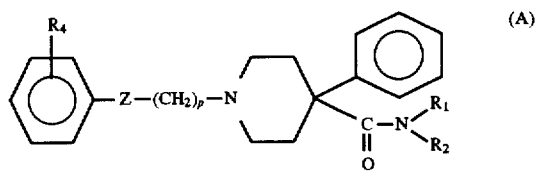

a process for their preparation and their use in the manufacture of pharmaceutical preparations. The new compounds have both local anaesthetic and analgesic effect.

28 Claims, No Drawings

COMPOUNDS WITH ANALGESIC AND LOCAL ANAESTHETIC EFFECT

This application is the national phase of PCT/SE95/00106, filed on Feb. 3, 1995 issued as WO95/21821 on Aug. 17, 1995.

FIELD OF THE INVENTION

The present invention is directed to new compounds having both local anaesthetic and analgesic effect, a process for their preparation and their use in the manufacture of pharmaceutical preparations.

BACKGROUND OF THE INVENTION

Pethidine is a frequently used analgesic, but its local anaesthetic effect is weak. The anaesthetic/analgesic effect of pethidine after spinal administration is often insufficient in both respects. Instead combinations of bupivacaine and fentanyl or morphine are being used. The opiate analgesics have several severe drawbacks, e.g. development of tolerance, addiction, risk for respiratory depression. There is, thus, a need for agents giving a local anaesthesia with a remaining analgesic effect having less side-effects than the currently used combinations. Such agents should be used after spinal or epidural injections as local anaesthetics intraoperatively. Thereafter the compounds would give good post-operative pain relief.

PRIOR ART

Hardy D. G. et al. describe in J.Med.Chem. 8, pp 847–851 (1965) the structure-activity relationship of certain analogues of pethidine, which are disclosed as having an analgesic activity. The Swedish patent 96980 describes 1-methyl-4-phenyl-piperidine-4-carboxylic acid and two amides thereof, but does not disclose any specific pharmaceutical effect, only that the compounds can be used in the manufacture of new drugs.

From WO SE90/00818 certain substituted 4-phenyl-piperidine-4-carboxamides are described as having both local anaesthetic and analgesic effects.

OUTLINE OF THE INVENTION

The novel compounds according to the present invention are defined by the following formulae (A):

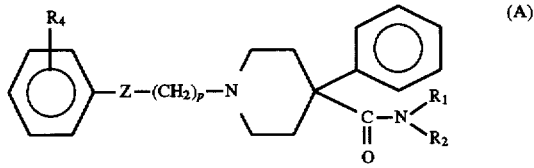

wherein Z is a group

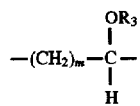

taken from the left to the right direction in formula (A) or a carbonyl group; and wherein:

a) $R_1$ is hydrogen or a straight or branched alkyl group with 1–3 carbon atoms, and
$R_2$ is a straight or branched alkyl group with 1–3 carbon atoms, or
b) $R_1$ and $R_2$ form together a chain —$(CH_2)_n$—, wherein n is 3, 4 or 5, or —$(CH_2)_2O(CH_2)_2$—;
m is 0–1;
p is 1–2;
$R_3$ is hydrogen or —$COCH_3$; and
$R_4$ is hydrogen, —$CH_3$, —OH or —$OCH_3$, with the proviso that when Z is a carbonyl group, p is 2, as well as the pharmaceutically acceptable salts of the compounds of formulae (A).

$R_4$ may be present in 2-, 3- or 4-position.

Preferred compounds according to the invention are those wherein $R_4$ (in the benzene ring which is coupled to the group Z) is in the 2-position and wherein $R_4$ is hydrogen, m is 0, $R_3$ is hydrogen, p is 2, and $R_1$ and $R_2$ are the same being an ethyl group; or $R_4$ is hydrogen, m is 0, $R_3$ is hydrogen, p is 2, $R_1$ is a methyl group and $R_2$ is an ethyl group; or $R_4$ is hydrogen, m is 0, $R_3$ is hydrogen, p is 2, and wherein $R_1$ and $R_2$ together form a chain —$(CH_2)$—$_4$; or $R_4$ is hydrogen, m is 0, $R_3$ is hydrogen, p is 2, $R_1$ is a methyl group and $R_2$ is an isopropyl group; or $R_4$ is a methoxy group, m is 0, $R_3$ is hydrogen, p is 2, $R_1$ is a methyl group and $R_2$ is an ethyl group; or $R_4$ is a methyl group, m is 0, $R_3$ is hydrogen, p is 2, $R_1$ is a methyl group and $R_2$ is an ethyl group; or $R_4$ is hydrogen, m is 0, $R_3$ is hydrogen, p is 1, and $R_1$ and $R_2$ are the same being an ethyl group.

Preferred salts according to the invention are pharmaceutically acceptable salts. The hydrochloride is especially preferred.

Citrate, methansulfonate and maleate are other examples of salts which can be used.

The compounds according to the present invention are more suitable to use in pain management, because they are less toxic and more effective as local anaesthetics and analgesics. Compounds of the formulae A and pharmaceutically acceptable salts thereof not only give an unexpectedly good effect as spinal and epidural anaesthetics, but also have an additional analgesic effect that lasts a long time after the anaesthetic effect has declined. Thus no combination of active compounds need to be given and the risks connected with these combinations can be avoided. The compounds also give an unexpectedly superior effect to the known compounds having this kind of combination effects.

The most preferred compounds according to the invention known at present, are the compounds according to Example 13 and Example 6A, i.e. compounds of the formula XIII, and compounds of the formula VI wherein $R_4$ is H, $R_1$ and $R_2$ are both —$C_2H_5$;
$R_4$ is H, $R_1$ is —$CH_3$ and $R_2$ is —$C_2H_5$;
$R_4$ is H and $R_1+R_2$ is —$(CH_2)_4$;
$R_4$ is H, $R_1$ is —$CH_3$ and $R_2$ is isopropyl;
$R_4$ is 2-$OCH_3$, $R_1$ is —$CH_3$ and $R_2$ is —$C_2H_5$;
$R_4$ is 2—$CH_3$, $R_1$ is —$CH_3$ and $R_2$ is —$C_2H_5$;

Preparation

For preparing the substituted piperidine-4-carboxamides of formula (A) according to the invention, the compounds could be divided into six groups which were prepared according to Schemes 1–5.

The first group, aromatically unsubstituted 1-(3-acetoxy-3-phenyl-propyl)-4-phenyl-piperidine-4-carboxamides (V), and the second group 1-(3-hydroxy-3-phenyl-propyl)-4- phenyl-piperidine-4-carboxamides (VI), were prepared according to the following reaction scheme:

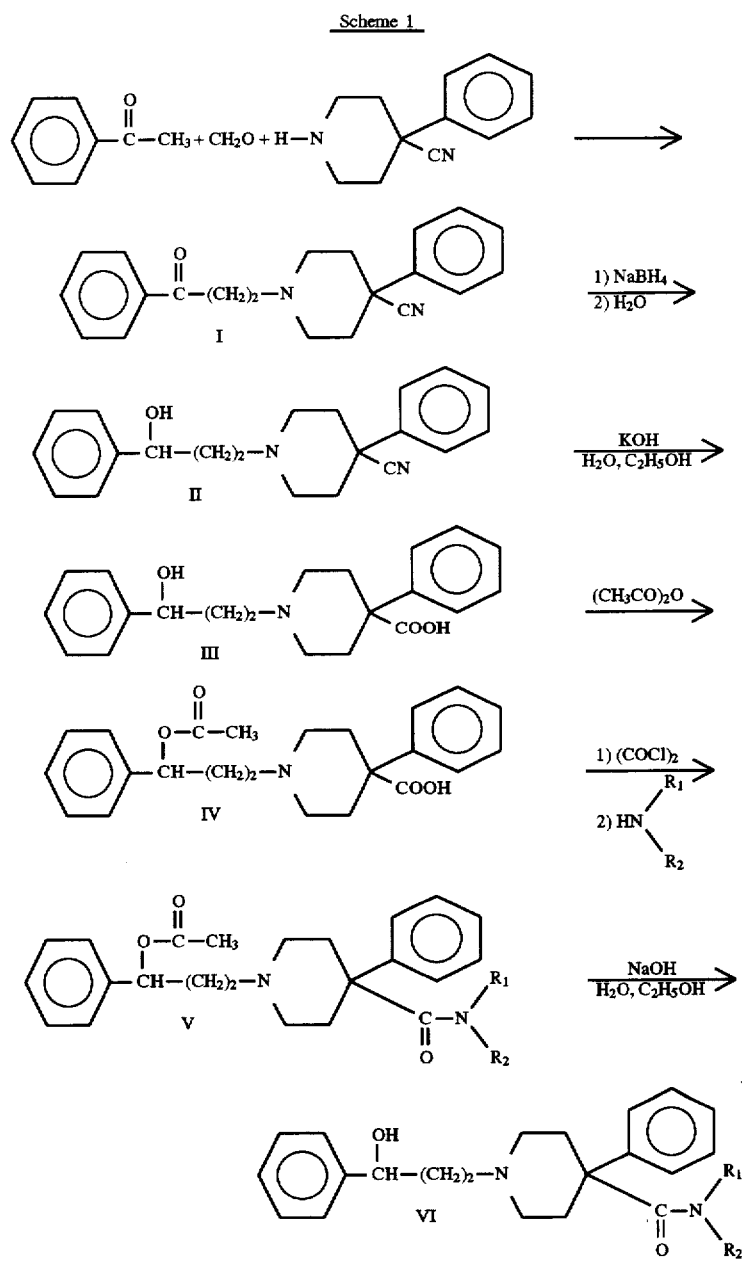

wherein $R_1$ and $R_2$ are as defined above.

The aminoketone I was prepared by a Mannich reaction of 4-phenyl-piperidine-4-carbonitrile with formaldehyde and acetophenone. The carbonyl group of I was reduced with sodium borohydride to give the secondary alcohol II. Hydrolysis of the cyano group under alkaline conditions gave the amino acid III. The hydroxyl group was acetylated, and the carboxylic acid IV was converted to the appropriate amide V via the acid chloride. Selective alkaline hydrolysis of the ester group of compounds V yielded the corresponding secondary alcohols VI.

Enantiomeric pure forms of compound VI, wherein $R_1$ is —$CH_3$ and $R_2$ is —$C_2H_5$ or $R_1$ and $R_2$ are the same being —$C_2H_5$ were prepared according to the following reaction scheme:

Scheme 2

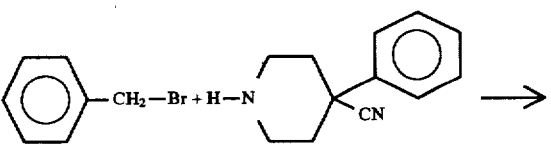

Scheme 2 -continued

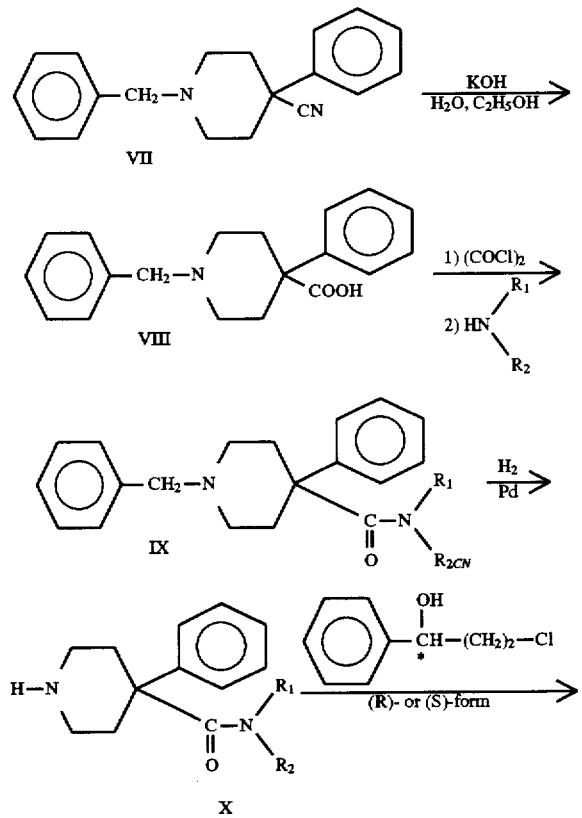

4-Phenyl-piperidine-4-carbonitrile was benzylated to give the aminonitrile VII, which was hydrolyzed under alkaline conditions to the amino acid VIII. The acid was converted to the appropriate amide IX via the acid chloride. Hydrogenolysis of the benzylamines in the presence of palladium catalyst gave the secondary amines X, which were alkylated with either (R)- or (S)-3-chloro-1-phenyl-1-propanol to give the two enantiomeric pairs of VI wherein $R_1$ is —$CH_3$ and $R_2$ is —$C_2H_5$ or $R_1$ and $R_2$ are the same being —$C_2H_5$.

Aromatically substituted piperidine-4-carboxamides wherein $R_1$ is —$CH_3$, $R_2$ is —$C_2H_5$ and $R_4$ is —$CH_3$, —OH or —$OCH_3$ comprise, together with compound XI wherein $R_1$ and $R_2$ are the same being —$C_2H_5$, and $R_4$ is hydrogen, the third (ketones XI) and fourth (alcohols VI) groups of new compounds. These were prepared according to the following reaction scheme:

Scheme 3

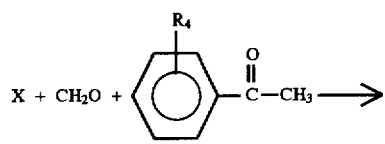

Scheme 3 -continued

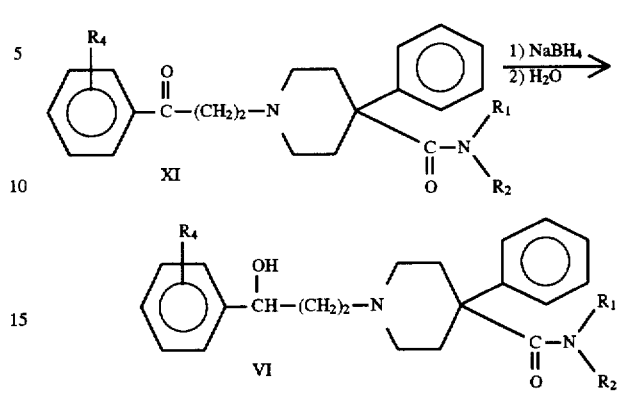

A Mannich reaction between the secondary amine X, wherein $R_1$ is —$CH_3$ and $R_2$ is —$C_2H_5$ or $R_1$ and $R_2$ are the same being —$C_2H_5$, formaldehyde and the appropriate benzophenone, with $R_4$ being hydrogen, —$CH_3$ or —$OCH_3$, gave the ketones XI. The carbonyl group of the aromatically substituted ketones XI ($R_4$ is —$CH_3$, —$OCH_3$ or —OH) was reduced with sodium borohydride to give the alcohols VI. Compound XI wherein $R_4$ is 2-hydroxy was prepared from the corresponding methoxy compound by demethylation with boron tribromide.

1-(2-Hydroxy-2-phenyl-ethyl)-4-phenyl-piperidine-4-carboxylic acid diethylamide (XIII), the fifth type of new compounds, was prepared according to the following reaction scheme:

Scheme 4

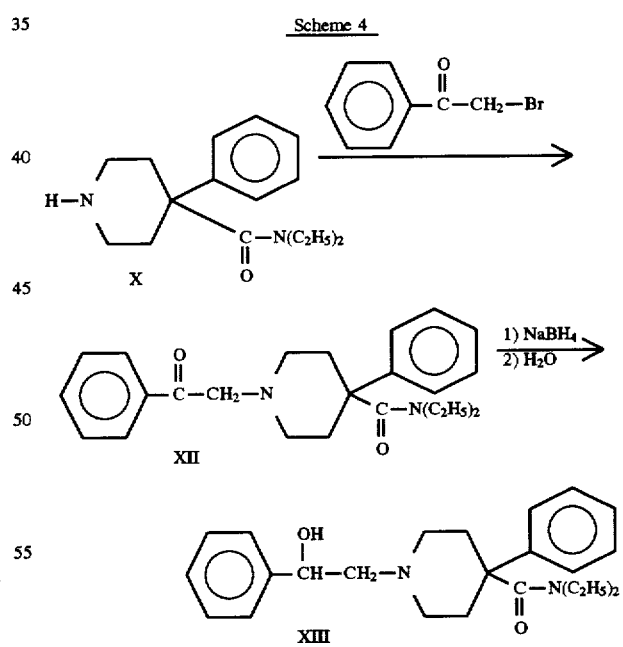

The secondary amine X wherein $R_1$ and $R_2$ are the same being —$C_2H_5$ was alkylated with phenacyl bromide to give the ketone XII, which was reduced with sodium borohydride to the secondary alcohol XIII.

The sixth group of compounds, 1-(2-hydroxy-3-phenyl-propyl)-4-phenyl-piperidine-4-carboxamides (XVIII) were prepared according to the following reaction scheme:

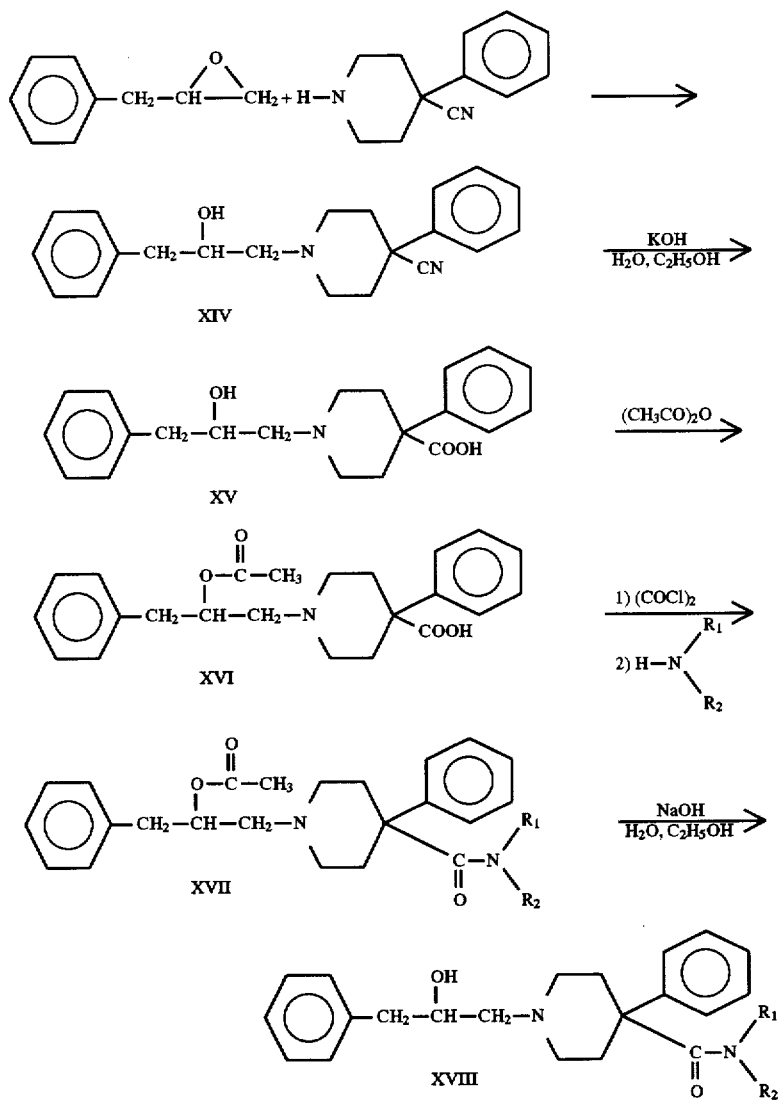

Scheme 5 wherein $R_1$ and $R_2$ are as defined above.

4-Phenyl-piperidine-4-carbonitrile was alkylated with (2,3-epoxypropyl)benzene to give the secondary alcohol XIV. Compounds XV, XVI, XVII and XVIII were prepared as described for compounds III, IV, V and VI respectively.

DETAILED DESCRIPTION OF THE PREPARATIONS

The following examples (Arabic numerals) describe in detail the preparation of the compounds (referred to by the same Roman numeral) according to the invention.

EXAMPLE 1

Preparation of 1-(3-oxo-3-phenyl-propyl)-4-phenyl-piperidine-4-carbonitrile
(Compound I)

A mixture of 4-phenyl-piperidine-4-carbonitrile hydrochloride (41.6 g, 187 mmol), formaldehyde (8.4 g, 280 mmol), acetophenone (33.6 g, 280 mmol) and 37% hydrochloric acid (2 ml) in ethanol (500 ml) was refluxed for 48 h. After cooling precipitated material was collected by filtration, yielding 40.0 g of the hydrochloride with m.p. 207°–210° C.

EXAMPLE 2

Preparation of 1-(3-hydroxy-3-phenyl-propyl)-4-phenyl-piperidine-4-carbonitrile
(Compound II)

The ketone I (48.2 g, 136 mmol) and sodium borohydride (20.0 g, 526 mmol) suspended in methanol (500 ml) was heated at 50° C. for 15 h. The solvent was evaporated and 2N hydrochloric acid (150 ml) was slowly added. The solution was then alkalized with 5N sodium hydroxide and extracted with three portions of chloroform (3×100 ml). The combined extracts were dried over potassium carbonate, filtered and the solvent was evaporated. Yield 41.0 g, with m.p. 109°–112° C.

EXAMPLE 3

Preparation of 1-(3-hydroxy-3-phenyl-propyl)-4-phenyl-piperidine-4-carboxylic acid (Compound III)

A solution of the nitrile II (20.3 g, 63 mmol) and potassium hydroxide (17.5 g, 313 mmol) in ethanol (50 ml) and water (80 ml) was heated in an autoclave at 140° C. for 6 h. After cooling the solution was evaporated to one third of its original volume and then acidified with hydrochloric acid to pH 2. The precipitate was collected by filtration. Yield 22.0 g of the hydrochloride with m.p. 280° C.

EXAMPLE 4

Preparation of 1-(3-acetoxy-3-phenyl-propyl)-4-phenyl-piperidine-4-carboxylic acid
(Compound IV)

A mixture of compound III (11.3 g, 30 mmol), acetic anhydride (200 ml) and 4-dimethylaminopyridine (0.3 g) was heated at 50° C. for 15 h. The solvent was evaporated and the residue was carefully dried at 80° C. in a vacuum cabinet and then recrystallized from dioxane. Yield 10.2 g of the hydrochloride with m.p. 189°–193° C.

EXAMPLE 5

Preparation of 1-(3-acetoxy-3-phenyl-propyl)-4-phenyl-piperidine-4-carboxamides
(Compounds V)

Oxalyl chloride (6 ml) was added dropwise with stirring to a suspension of the piperidinecarboxylic acid IV (5.0 g, 12 mmol) in dichloromethane (100 ml). The reaction mixture was stirred at 50° C. for 2 h. The solvent was evaporated, a few ml of toluene were added and the solvent was evaporated again. The residue was dissolved in dichloromethane (50 ml) and the solution was added dropwise with stirring to a solution of the appropriate amine (36 mmol) in dichloromethane (20 ml), cooled in ice-water. The reaction mixture was stirred at room temperature for 4 h. The solvent was evaporated and the residue was shaken between dilute sodium hydroxide (20 ml) and dichloromethane (3×20 ml). The organic extract was dried over potassium carbonate, filtered and evaporated to dryness. Hydrochlorides were prepared by addition of hydrogen chloride in diethyl ether to etheral solutions of the amines. The compounds were recrystallized from the appropriate solvent (Table 1).

EXAMPLE 6A

Preparation of 1-(3-hydroxy-3-phenyl-propyl)-4-phenyl-piperidine-4-carboxamides
(Compounds VI)

A suspension of the ester V (12 mmol) in 2N sodium hydroxide (60 ml) and ethanol (40 ml) was heated at 70° C. for 3 h. The solution was evaporated to half its original volume and then extracted with three portions of diethyl ether (3×50 ml). The ether extract was dried over potassium carbonate, filtered, and the hydrochloride was prepared as described in Example 5. The compounds were purified by recrystallization from the indicated solvent (Table 1).

EXAMPLE 7

Preparation of 1-benzyl-4-phenyl-piperidine-4-carbonitrile
(Compound VII)

A mixture of 4-phenyl-piperidine-4-carbonitrile (41.4 g, 223 mmol), benzyl bromide (41.9 g, 245 mmol) and sodium carbonate (29.7 g, 281 mmol) in 1-butanol (300 ml) was stirred at room temperature for 12 h. The solvent was evaporated and 1N sodium hydroxide (100 ml) was added. The water phase was extracted three times with dichloromethane (3×150 ml). The combined extracts were dried over potassium carbonate, filtered and evaporated to dryness. Yield 59.0 g with m.p. 76°–79° C.

EXAMPLE 8

Preparation of 1-benzyl-4-phenyl-piperidine-4-carboxylic acid
(Compound VIII)

The nitrile VII (20.0 g, 73 mmol) was hydrolyzed in an autoclave as described in Example 3. The reaction mixture was evaporated to one third of its original volume and neutralized with hydrochloric acid. Precipitated material was collected by filtration, yielding 18.6 g of the amino acid with m.p. 288°–290° C.

EXAMPLE 9

Preparation of 1-benzyl-4-phenyl-piperidine-4-carboxamides
(Compounds IX)

The carboxylic acid VIII was converted to the appropriate amide as described for compounds V. The amide with $R_1$ being —$CH_3$ and $R_2$ being —$C_2H_5$ was isolated as the free base, recrystallized from ethyl acetate and obtained in 62% yield with m.p. 108°–112° C. The amide wherein $R_1$ and $R_2$ are the same being —$C_2H_5$ was isolated as the hydrochloride and recrystallized from a mixture of acetonitrile and ethyl acetate. Yield 54% with m.p. 204°–206° C.

EXAMPLE 10

Preparation of 4-phenyl-piperidine-4-carboxamides
(Compounds X)

A solution of the appropriate tertiary amine IX (13 mmol, obtained from the hydrochloride in the usual way) in methanol (200 ml) was hydrogenated at atmospheric pressure in the presence of 5% palladium on activated carbon (100 mg) until the calculated amount of hydrogen had been consumed. The catalyst was removed by filtration and the solvent was evaporated. The hydrochlorides were prepared as described in Example 5 and recrystallized from acetonitrile. The amide with $R_1$ being —$CH_3$ and $R_2$ being —$C_2H_5$ was obtained in 94% yield with m.p. 214°–217° C., and the amide wherein $R_1$ and $R_2$ are the same being —$C_2H_5$ in 91% yield with m.p. 238°–240° C.

EXAMPLE 6B

Preparation of optically active 1-(3-hydroxy-3-phenyl-propyl)-4 phenyl-piperidine-4-carboxamides
(Compounds VI wherein $R_1$ is —$CH_3$ and $R_2$ is —$C_2H_5$ or $R_1$ and $R_2$ are the same being —$C_2H_5$).

A mixture of the appropriate amine X (4.0 mmol, obtained from the hydrochloride in the usual way), (R)-3-chloro-1-phenyl-1-propanol (0.70 g, 4.12 mmol; prepared according to Brown H C et al in J.Org.Chem. 53 pp. 2916–2920 (1988)) or the (S)-enantiomer (of commercial origin), sodium carbonate (0.46 g, 4.3 mmol) and potassium iodide (50 mg) in 1-butanol (20 ml) was refluxed for 30 h. The solvent was evaporated and 0.5N sodium hydroxide (10 ml) was added. The water phase was extracted three times with diethyl ether (3×20 ml). The combined extracts were dried over potassium carbonate and filtered. The hydrochloride was precipitated as described in Example 5. The salts were recrystallized from the indicated solvent (Table 1). The optical rotations [$[\alpha]_D^{20}$, (c=mg/ml)] obtained in absolute ethanol are as listed:

| $R_1$ | $R_2$ | (R)-VI | (S)-VI |
|---|---|---|---|
| $CH_3$ | $C_2H_5$ | +22.2° (10.0) | −23.4° (10.0) |
| $C_2H_5$ | $C_2H_5$ | +20.4° (2.8) | −21.8° (2.8) |

TABLE 1

Hydrochlorides of compounds V and VI

| $R_1$ | $R_2$ | m.p. of V [°C.], (xx solvent), yield % | m.p. of VI [°C.], (xx solvent), yield % |
|---|---|---|---|
| H | $C_3H_7$ | 158–160, (b), 60 | 185–190, (a), 75 |
| $CH_3$ | $CH_3$ | 197–198, (b), 69 | 192–194, (a), 51 |
| $CH_3$ | $C_2H_5$ | 208–210, (b), 45 | [racemic]: 149, (a), 45 |
| $CH_3$ | $C_2H5$ | — | (R): 178–181, (a), 58 |
| $CH_3$ | $C_2H_5$ | — | (S): 179–181, (a), 53 |
| $C_2H_5$ | $C_2H_5$ | 218–220, (b), 96 | [racemic]: 135–138, (b), 80 |
| $C_2H_5$ | $C_2H_5$ | — | (R): 169–170, (b), 60 |
| $C_2H_5$ | $C_2H_5$ | — | (S): 165–167, (b), 55 |
| $CH_3$ | $CH(CH_3)_2$ | 195–197, (b), 60 | 143–147, (b), 45 |
| $C_2H_5$ | $CH(CH_3)_2$ | 198–204, (b), 50 | 168–171, (a), 45 |
| $CH(CH_3)_2$ | $CH(CH_3)_2$ | 217–219, (b), 45 | 148–152, (b), 21 |
| —$(CH_2)_3$— | | 175–182, (b), 73 | 214–215, (b), 75 |
| —$(CH_2)_4$— | | 197–201, (b), 45 | 232–235, (a), 46 |
| —$(CH_2)_5$— | | 190–191, (b), 31 | 188–190, (b), 74 |
| —$(CH_2)_2O(CH_2)_2$— | | 221–222, (b), 32 | 210–212, (a), 67 |

Recrystallization solvent:
(a) = acetonitrile
(b) = ethyl acetate

EXAMPLE 11A
Preparation of 1-(3-oxo-3-phenyl-propyl)-4-phenyl-piperidine-4-carboxamides
(Compounds XI)

Mannich reactions performed as described in Example 1 between the amine X with $R_1$ being —$CH_3$ and $R_2$ being —$C_2H_5$ or $R_1$ and $R_2$ are the same being —$C_2H_5$, formaldehyde, and the appropriate acetophenone with $R_4$ being hydrogen, 2-$OCH_3$, 3-$OCH_3$, 4-$OCH_3$ or 2-$CH_3$ gave the corresponding ketones XI. Compound XI wherein $R_1$ and $R_2$ are the same being —$C_2H_5$ and $R_4$ being hydrogen, was recrystallized from acetonitrile. Yield 70 %, with m.p. 189°–192° C. The aromatically substituted ketones XI were recrystallized from the indicated solvent and had the m.p.s given in Table 2.

EXAMPLE 11B
Preparation of 1-[3-(2-hydroxy-phenyl)-3-oxo-propyl]-4-phenyl-piperidine-4-carboxylic acid ethyl-methyl-amide
(Compound XI wherein $R_1$ is —$CH_3$, $R_2$ is —$C_2H_5$ and $R_4$ is 2-OH)

To a solution of compound XI wherein $R_4$ is 2-$OCH_3$ (1.3 g, 2.9 mmol) in dichloromethane (25 ml) cooled in ice-water was added 0.5M boron tribromide (15 ml, 7.5 mmol) in dichloromethane, and the mixture was stirred at room temperature for 24 h. The dichloromethane solution was shaken with dilute ammonia and the organic phase was separated and dried over sodium sulfate. The solvent was evaporated and the residual base converted to hydrochloride as described in Example 5 (Table 2). Yield 1.0 g.

EXAMPLE 6C
Preparation of aromatically substituted 1-(3-hydroxy-3-phenyl-propyl)-4-phenyl-piperidine-4-carboxylic acid ethyl-methyl-amides (Compounds VI)

The ketone XI wherein $R_4$ is 2-$OCH_3$, 3-OCH3, 4-$OCH_3$, 2-$CH_3$ or 2-OH (1 mmol) and sodium borohydride (6 mmol) were suspended in tetrahydrofurane and stirred at room temperature for 48 h. The product was isolated as described in Example 2, and the hydrochloride was prepared as described in Example 5. Recrystallization solvents and m.p.s are given in Table 2.

TABLE 2

Hydrochlorides of the aromatically substituted piperidine-4-carboxylic acid ethyl-methyl-amides XI and VI.

| $R_4$ | m.p. of XI [°C.], (xx solvent), yield % | m.p. of VI [°C.], (xx solvent), yield % |
|---|---|---|
| 2-$OCH_3$ | 208–210, (a), 54 | 176–180, (a), 75 |
| 3-$OCH_3$ | 205–207, (a), 50 | 124–127, (b), 75 |
| 4-$OCH_3$ | 208–209, (a), 36 | — |
| 2-$CH_3$ | 198–200, (a), 50 | 185–189, (b), 60 |
| 2-OH | 185–187, (a), 79 | 206–210, (a), 50 |

Recrystallization solvent:
(a) = acetonitrile
(b) = ethyl acetate

EXAMPLE 12
Preparation of 1-(2-oxo-2-phenyl-ethyl)-4-phenyl-piperidine-4-carboxylic acid diethylamide
(Compound XII)

A mixture of the secondary amine X wherein $R_1$ and $R_2$ are the same being —$C_2H_5$ (1.0 g, 3.8 mmol), phenacyl bromide (0.81 g, 4.1 mmol) and sodium carbonate (1.0 g, 9.4 mmol) in 1-butanol was stirred at room temperature for 5 days. The product was isolated as described in Example 7. The hydrochloride was prepared as described in Example 5. Recrystallization from a mixture of acetonitrile and dioxane gave 0.8 g with m.p. 209°–212° C.

EXAMPLE 13
Preparation of 1-(2-hydroxy-2-phenyl-ethyl)-4-phenyl-piperidine-4-carboxylic acid diethylamide
(Compound XIII)

A mixture of the ketone XII (0.5 g, 1.2 mmol, converted to the free amine in the usual way) and sodium borohydride (0.3 g, 7.9 mmol) in tetrahydrofurane (20 ml) was stirred at room temperature for 4 days. The product was isolated as in Example 2. The hydrochloride was precipitated as described in Example 5 and the product was recrystallized twice from a mixture of acetonitrile and ethyl acetate. Yield 0.2 g with m.p. 203°–205° C.

EXAMPLE 14
Preparation of 1-(2-hydroxy-3-phenyl-propyl)-4-phenyl-piperidine-4-carbonitrile
(Compound XIV)

A mixture of 4-phenyl-piperidine-4-carbonitrile (6.3 g, 34 mmol) and (2,3-epoxypropyl)benzene (5.0 g, 37 mmol) in dioxane was refluxed for seven days. The solvent was evaporated and the residue was shaken between dilute sodium hydroxide and diethyl ether. The ether extract was dried over potassium carbonate, filtered and the product was converted to the hydrochloride as described in Example 5. Recrystallization from a mixture of ethanol and acetonitrile gave 10.0 g with m.p. 246°–249° C.

EXAMPLE 15

Preparation of 1-(2-hydroxy-3-phenyl-propyl)-4-phenyl-piperidine-4-carboxylic acid (Compound XV)

The nitrile XIV (10.0 g, 28.1 mmol) was hydrolyzed in an autoclave as described in Example 8. Yield 9.5 g of the amino acid with m.p. 288°–290° C.

EXAMPLE 16

Preparation of 1-(2-acetoxy-3-phenyl-propyl)-4-phenyl-piperidine-4-carboxylic acid (Compound XVI)

The secondary alcohol XV (2.0 g, 5.9 mmol) was acetylated as described in Example 4. Recrystallization from dioxane gave 2.0 g of the amino acid with m.p. 179°–182° C.

EXAMPLE 17

Preparation of 1-(2-acetoxy-3-phenyl-propyl)-4-phenyl-piperidine-4-carboxamides (Compounds XVII)

The carboxylic acid XVI was converted to the appropriate amides as described for compounds V. The hydrochlorides were recrystallized from ethyl acetate. The amide wherein $R_1$ is —$CH_3$ and $R_2$ is —$C_2H_5$ was obtained in 83% yield with m.p. 185°–187° C., and the amide wherein $R_1$ and $R_2$ are the same being —$C_2H_5$ in 75% yield with m.p. 164°–167° C.

EXAMPLE 18

Preparation of 1-(2-hydroxy-3-phenyl-propyl)-4-phenyl-piperidine-4-carboxamides (Compounds XVIII)

The esters XVII were hydrolyzed as described in Example 6A. The hydrochlorides were recrystallized from a mixture of acetonitrile and ethyl acetate. Compound XVIII wherein $R_1$ is —$CH_3$ and $R_2$ is —$C_2H_5$ was obtained in 60% yield with m.p. 171°–175° C., and XVIII wherein $R_1$ and $R_2$ are the same being —$C_2H_5$ in 55% yield with m.p. 166°–169° C.

Pharmaceutical Preparations

For the preparation of pharmaceutical formulations one of the new compounds is dissolved in a liquid diluent, which is suitable for injection, e.g. physiological saline. The preparations used are aqueous solutions which contain between 0.1–100 mg/ml, preferably 3–20 mg/ml of the active compund calculated as the hydrochloride salt.

Biological Studies

Spinal Anaesthesia

The compounds according to the invention were tested for spinal anaesthesia in the mouse. There were six animals in each group. As reference compund pethidine was used.

Mean duration (min) of motor block and full analgesia (tail-flick) in mice after intrathecal (spinal) injection of 5 μl of the test solution was measured. The durations were calculated from the time of injection.

Discussion

As the local anaesthetic effect is potently combined with an analgesic effect, the compounds according to the invention should be more useful than pethidine. It should also be possible to replace the frequently used combinations of one analgesic and one anaesthetic agent.

What is claimed is:

1. A compound, or pharmaceutically acceptable salt thereof, wherein said compound has the chemical structure of formula (A):

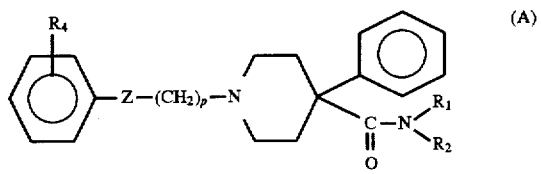

and wherein a) Z is a group

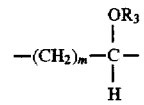

taken from the left to the right direction in formula (A), or a carbonyl group;

b) $R_1$ is hydrogen or a straight or branched alkyl group with 1–3 carbon atoms and $R_2$ is a straight or branched alkyl group with 1–3 carbon atoms; or i) $R_1$ and $R_2$ together form a chain —$(CH_2)n$—, wherein n is 3, 4 or 5; or ii) $R_1$ and $R_2$ together form a chain —$(CH_2)_2O(CH_2)_2$—;

c) m is 0–1;

d) p is 1–2;

e) $R_3$ is hydrogen or —$COCH_3$; and f) $R_4$ is hydrogen, —$CH_3$, —OH or —$OCH_3$;

g) with the proviso that when Z is a carbonyl group, p is 2 and either;

i) $R_1$ and $R_2$ together form a chain —$(CH_2)n$— wherein n is 3;

ii) $R_4$ is —OH; and with the proviso that when p=2, m=0, or p=1, m=1, $R_3$ and $R_4$ cannot both be hydrogen.

2. The compound of claim 1, wherein:

a) Z is:

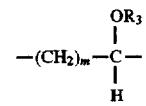

b) $R_3$ is:

c) $R_4$ is hydrogen;

d) m is 0; and e) p is 2.

3. The compound of claim 1, wherein:

a) Z is:

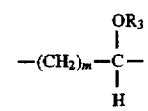

b) $R_3$ is hydrogen;

c) m is 0; and d) p is 2.

4. The compound of claim 1, wherein $R_4$ is in the 2-position.

5. The compound of claim 3, wherein:
 a) $R_1$ is an ethyl group; and
 b) $R_2$ is an ethyl group.

6. The compound of claim 3, wherein:
 a) $R_1$ is a methyl group; and
 b) $R_2$ is an ethyl group.

7. The compound of claim 3, wherein $R_1$ and $R_2$ together form a chain —$(CH_2)_4$—.

8. The compound of claim 3, wherein:
 a) $R_1$ is a methyl group; and
 b) $R_2$ is an isopropyl group.

9. The compound of either claim 1 or claim 4, wherein:
 a) $R_1$ is a methyl group;
 b) $R_2$ is an ethyl group;
 c) $R_3$ is hydrogen;
 d) $R_4$ is a methoxy group;
 e) m is 0; and
 f) p is 2.

10. The compound of either claim 1 or claim 4, wherein:
 a) $R_1$ is a methyl group;
 b) $R_2$ is an ethyl group;
 c) $R_3$ is hydrogen;
 d) R4 is a methyl group;
 e) m is 0; and
 f) p is 2.

11. The compound of claim 1, wherein:
 a) $R_1$ is an ethyl group;
 b) $R_2$ is an ethyl group;
 b) $R_3$ is hydrogen;
 c) $R_4$ is hydrogen;
 d) m is 0; and
 e) p is 1.

12. The compound of claim 3, wherein:
 a) said compound is in the (R)-form;
 b) $R_1$ is a methyl group; and
 c) $R_2$ is an ethyl group.

13. The compound of claim 3, wherein:
 a) said compound is in the (R)-form;
 b) $R_1$ is a ethyl group; and
 c) $R_2$ is an ethyl group.

14. The compound of claim 3, wherein:
 a) said compound is in the (S)-form;
 b) $R_1$ is a methyl group; and
 c) $R_2$ is an ethyl group.

15. The compound of claim 3, wherein:
 a) said compound is in the (S)-form; and
 b) $R_1$ is an ethyl group; and
 c) $R_2$ is an ethyl group.

16. The compound of claim 1, wherein said pharmaceutically acceptable salt is a hydrochloride.

17. The compound of claim 2, wherein said compound is in the form of a hydrochloride.

18. The compound of claim 1, wherein said compound is in a form of a pharmaceutically acceptable salt suitable for use in therapy.

19. A pharmaceutical composition comprising the compound or pharmaceutically acceptable salt thereof of formula (A) according to claim 1 as an active ingredient, and further comprising a pharmaceutically acceptable carrier.

20. The pharmaceutical composition of claim 19, wherein the concentration of said compound or pharmaceutically acceptable salt thereof is between about 0.1 mg/ml and about 100 mg/ml.

21. The pharmaceutical composition of claim 20, wherein said concentration is between about 3 mg/ml and about 20 mg/ml.

22. A method for controlling nerve blockade in a subject, comprising administering the pharmaceutical composition of claim 19.

23. The method of claim 22, wherein said pharmaceutical composition is administered epidurally or intrathecally.

24. A process for the preparation of a compound of formula (A) according to claim 1, and pharmaceutically acceptable salts thereof, comprising the steps of:

(a) preparing an aminoketone of formula I:

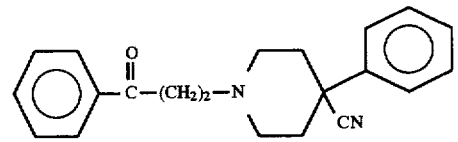

by a Mannich reaction of 4-phenyl-piperidine-4-carbonitrile with formaldehyde and acetophenone;

b) reducing the carbonyl group of said aminoketone of formula I with sodium borohydride to give a secondary alcohol of formula II:

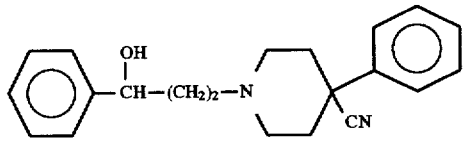

c) hydrolyzing the cyano group of said secondary alcohol of formula II under alkaline conditions to produce an amino acid of formula III:

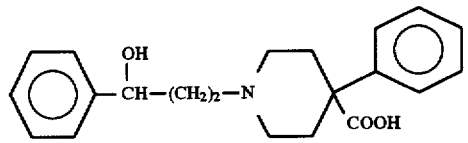

d) acetylating the hydroxyl group of said amino acid of formula III to form an ester of formula IV:

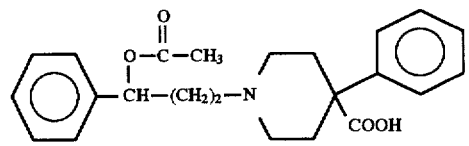

e) converting the carboxylic group of said ester of formula IV to an amide of formula V via the acid chloride:

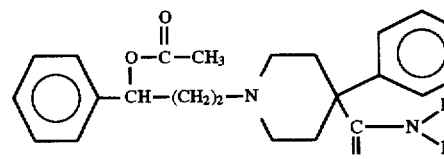

f) performing selective alkaline hydrolysis of the ester group of said amide of formula V to yield a compound of formula VI:

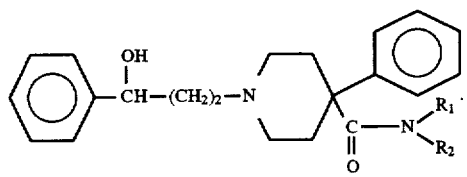
IV

25. A process for the preparation of a compound of formula (A) according to claim 1, and pharmaceutically acceptable salts thereof, comprising the steps of:

a) benzylating 4-phenyl-piperidine-4-carbonitrile to give the aminonitrile of formula VII:

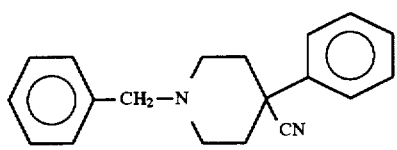
VII b) hydrolyzing said aminonitrile of formula VII under alkaline conditions to give the amino acid of formula VIII:

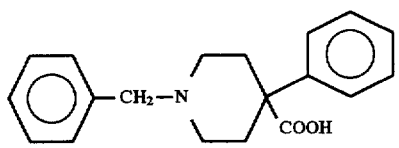
VIII c) converting said amino acid of formula VIII to an amide of formula IX via the acid chloride:

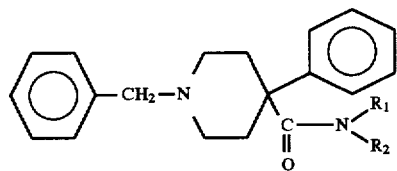
IX d) performing hydrogenolysis of said amide of formula IX in the presence of a palladium catalyst to give a secondary amine of formula X:

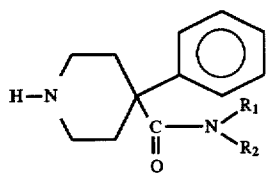
X e) producing a compound of formula (A) according to claim 1 by either:
  i) alkylating said secondary amine of formula X with (R)- or (S)-3-chloro-1-phenyl-1-propanol, to give the two enantiomeric isomers of formula VI;
  ii) subjecting said secondary amine of formula X to a Mannich reaction with formaldehyde and a benzophenone to produce a compound of formula XI:

XI and then reducing the carbonyl group of said compound of formula XI with sodium borohydride to produce a compound of formula VI; or
  iii) alkylating said secondary amine of formula X with phenacyl bromide to give a ketone of formula XII:

XII and then reducing said ketone of formula XII with sodium borohydride to produce a secondary alcohol of formula XIII:

XIII

26. A process for the preparation of a compound of formula (A) according to claim 1, and pharmaceutically acceptable salts thereof, comprising the steps of:
a) alkylating 4-phenyl-piperidine-4-carbonitrile with (2,3-epoxypropyl) benzene to produce a secondary alcohol of formula XIV:

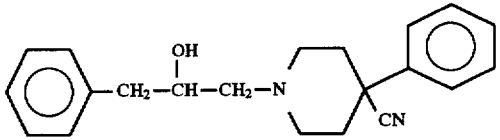
XIV b) converting said secondary alcohol of formula XIV to a compound of formula XVIII:

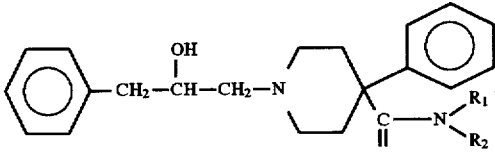
XVIII

27. The process of any one of claims 24, 25 or 26, further comprising converting the compound produced in the final step of each claim into a pharmaceutically acceptable salt.

28. A method of treating a subject suffering from pain, comprising administering to said subject a compound according to claim 1, or a pharmaceutically acceptable salt thereof in an amount sufficient to obtain an analgesic or local anaesthetic effect.

* * * * *

UNITED STATES PATENT AND TRADEMARK OFFICE
CERTIFICATE OF CORRECTION

PATENT NO. : 5,756,520
DATED : 5/26/98
INVENTOR(S) : Ask et al.

It is certified that error appears in the above-identified patent and that said Letters Patent is hereby corrected as shown below:

Column 14, delete lines 31-37, and insert therefore:

g) with the proviso that when Z is a carbonyl group, p is 2 and either:

i) $R_1$ and $R_2$ together form a chain- $(CH_2)n$- wherein n is 3; or ii) $R_4$ is –OH;

h) and with the further proviso that when p=2, m=0 or p=1, m=1, then $R_3$ and $R_4$ cannot both be hydrogen.

Signed and Sealed this

Twenty-third Day of March, 1999

Attest:

Q. TODD DICKINSON

Attesting Officer

Acting Commissioner of Patents and Trademarks